(12) United States Patent
Thomas et al.

(10) Patent No.: US 11,913,866 B2
(45) Date of Patent: Feb. 27, 2024

(54) SYSTEM AND DEVICE FOR ANALYZING FLUID FLOW IN UNCONVENTIONAL HYDRAULICALLY-FRACTURED POROUS MEDIA

(71) Applicant: Stratum Reservoir Intermediate, LLC, Houston, TX (US)

(72) Inventors: Forast Brent Thomas, Crossfield (CA); William Mackinnon Gibb, Crossfield (CA); Michael Steven Piwowar, Calgary (CA)

(73) Assignee: Stratum Reservoir Intermediate, LLC, Houston, TX (US)

( * ) Notice: Subject to any disclaimer, the term of this patent is extended or adjusted under 35 U.S.C. 154(b) by 0 days.

(21) Appl. No.: 17/576,428

(22) Filed: Jan. 14, 2022

(65) Prior Publication Data

US 2022/0136952 A1 May 5, 2022

Related U.S. Application Data

(63) Continuation of application No. 16/834,383, filed on Mar. 30, 2020, now Pat. No. 11,287,361.

(51) Int. Cl.
*G01N 15/08* (2006.01)
*G01N 33/24* (2006.01)
*E21B 49/00* (2006.01)

(52) U.S. Cl.
CPC ..... *G01N 15/0826* (2013.01); *G01N 15/0806* (2013.01); *G01N 33/24* (2013.01)

(58) Field of Classification Search
CPC ........ E21B 49/00; G01N 15/00; G01N 15/08; G01N 15/0806; G01N 15/0826; G01N 33/24
See application file for complete search history.

(56) References Cited

U.S. PATENT DOCUMENTS

| | | | |
|---|---|---|---|
| 8,701,766 B2 | 4/2014 | James | |
| 2016/0138394 A1* | 5/2016 | Brooks | .......... E21B 49/02 73/152.07 |
| 2018/0306736 A1 | 10/2018 | Li et al. | |

FOREIGN PATENT DOCUMENTS

| | | |
|---|---|---|
| CN | 102662044 | 9/2012 |
| CN | 104374637 | 2/2015 |
| CN | 106053240 | 10/2016 |
| CN | 110344826 | 10/2019 |

OTHER PUBLICATIONS

International Search Report and Written Opinion for Application No. PCT/US2021/024897 dated Jul. 20, 2021.

* cited by examiner

*Primary Examiner* — Nguyen Q. Ha
(74) *Attorney, Agent, or Firm* — Tumey L.L.P.

(57) ABSTRACT

A system for analyzing fluid flow in unconventional, hydraulically-fractured porous media. In one embodiment, the system comprises a reservoir test sample, wherein the reservoir test sample comprises a core barrel, annular fluid, a synthetic tubing, supporting layers, and a core sample stack, wherein the core sample stack comprises one or more core slots.

11 Claims, 4 Drawing Sheets

SYSTEM AND DEVICE FOR ANALYZING FLUID FLOW IN UNCONVENTIONAL HYDRAULICALLY-FRACTURED POROUS MEDIA

CROSS-REFERENCE TO RELATED APPLICATIONS

This application is a continuation application of U.S. patent application Ser. No. 16/834,383 filed Mar. 30, 2020, the entire contents of which is incorporated herein by reference thereto.

STATEMENT REGARDING FEDERALLY SPONSORED RESEARCH OR DEVELOPMENT

Not applicable.

BACKGROUND OF THE INVENTION

Field of the Invention

The present invention relates to oil and gas reservoir analysis equipment, and more particularly to oil and gas reservoir analysis equipment capable of experimentally analyzing fluid flow in an unconventional reservoir that may comprise hydraulically-fractured porous media.

Background of the Invention

Oil and gas reservoirs, which can be classified as conventional or unconventional, are subsurface pools of hydrocarbons contained within porous media or fractured rock formations in the earth. Conventional reservoirs are those in which the naturally occurring hydrocarbons, such as crude oil or natural gas, are trapped by overlying rock formations with permeability that is sufficiently high and therefore can produce oil and/or natural gas at economically viable rates. Unconventional reservoirs are those in which the hydrocarbons are trapped in place by rocks with low porosity and extremely low permeability, and will therefore not produce oil and natural gas at economically viable rates unless hydraulically fractured. The ability to understand and predict the behavior of both conventional and unconventional reservoirs can be highly beneficial in determining the production value of a well.

Currently, laboratory simulations and experimental evaluations performed for conventional reservoirs, may allow an operator to determine whether or not a well will produce a successful and economical flow of hydrocarbon streams from a reservoir to a wellbore. However, in unconventional reservoirs the flow of hydrocarbon streams can be more difficult to simulate and evaluate. In unconventional, hydraulically-fractured porous media, there are two fluid flow regimes worth evaluating: flow within a reservoir's fractures and flow between a reservoir's matrix and fractures. Due to the nature of unconventional, hydraulically-fractured porous media (low permeability, low porosity, and a low water saturation range) the two fluid flow regimes cannot be analyzed using standard simulation and evaluation equipment. Current equipment would require an unreasonable and inefficient amount of time to displace one pore volume of fluid in such porous media, as well as be incapable of incorporating the matrix-fracture regime of fluid flow.

Consequently, there is a need in the art for oil and gas reservoir analysis equipment capable of analyzing fluid flow in unconventional, hydraulically-fractured porous media in an efficient amount of time with the capability of incorporating the matrix-fracture regime of fluid flow.

BRIEF SUMMARY OF SOME OF THE PREFERRED EMBODIMENTS

These and other needs in the art are addressed in one embodiment by a fluid flow analysis system comprising a reservoir test sample, wherein the reservoir test sample comprises a core barrel, annular fluid, a synthetic tubing, a supporting layers, and a core sample stack, wherein the core sample stack comprises one or more core slots.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

Figure 1:
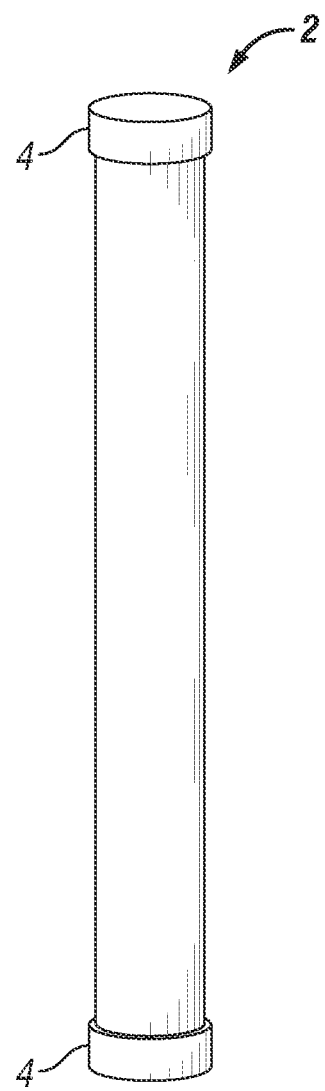
FIG. 1 illustrates an embodiment of a reservoir test sample from a perspective view.

FIG. 1 illustrates an embodiment of a reservoir test sample 2 from a perspective view. Reservoir test sample 2 may be a laboratory-scaled device configured for use with additional laboratory equipment in order to simulate the behavior of hydrocarbon streams in an oil and gas reservoir. The additional laboratory equipment (not illustrated) that may be used in executing fluid flow experiments are, without limitation, positive displacement pumps, high-pressure cylinders, visual cell(s), pressure transducers, a temperature gauge, gas chromatographs, a fluid separator, a pycnometer, a densitometer, or any combinations thereof. In embodiments, reservoir test sample 2 may allow for accurate and effective fluid flow analysis such as, without limitation, PVT, flow assurance, and water analysis of an oil and gas reservoir, particularly those of an unconventional nature which may comprise hydraulically-fractured porous media. Reservoir test sample 2 may be any suitable size and/or shape. In embodiments, reservoir test sample 2 may comprise a full-diameter cylindrical core or longitudinal slabs thereof that may be made into cylindrical shapes by inclusion of synthetic slabs of nylon and/or other impermeable material. Further, reservoir test sample 2 may be suitable for placement in a laboratory testing environment. For instance, the sample 2 may be placed for testing in an oven in which reservoir temperatures can be maintained. Temperatures reaching up to 400° F. may be simulated. In embodiments, as illustrated in FIG. 1, reservoir test sample 2 may be cylindrical. In embodiments, the size of reservoir test sample 2 may be dependent upon its internal components. In embodiments, reservoir test sample 2 may have flow heads 4 on each end of the sample. Flow heads 4 may allow for a sufficient seal to be established, which may thereby separate annular overburden pressure from pore pressure in the sample. Further, the additional laboratory equipment disclosed above may be connected to reservoir test sample 2 via flow heads 4.

Figure 2:
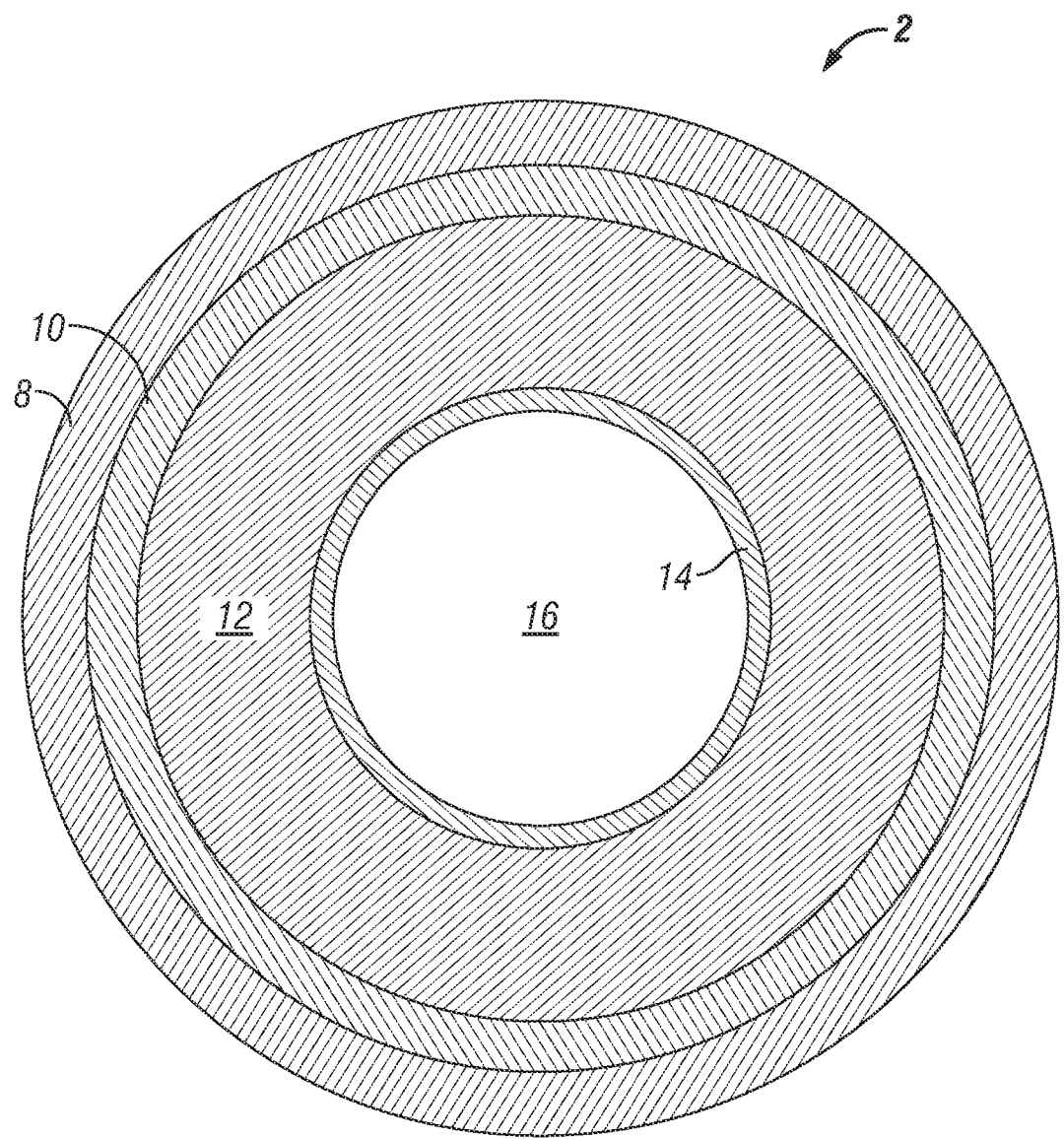
FIG. 2 illustrates an embodiment of a reservoir test sample from a radial cross-section view.

FIG. 2 illustrates a radial cross-section of an embodiment of reservoir test sample 2. Reservoir test sample 2 may comprise a core barrel 8, annular fluid 10, a synthetic tubing 12, supporting layers 14, and a core sample stack 16. In embodiments, core barrel 8 may be the outer most portion of reservoir test sample 2, such that annular fluid 10, synthetic tubing 12, supporting layers 14, and core sample stack 16 may be disposed within core barrel 8. Core barrel 8 may be any suitable shape and/or size capable of housing these components. In embodiments, core barrel 8 may be dimensioned according to the shape and size of core sample stack 16. Further, the amount of annular fluid 10 required in reservoir test sample 2 may influence the dimensions of core barrel 8. In embodiments, core barrel 8 may be any suitable material capable of withstanding high temperatures, high pressures, and harsh chemical. In embodiments, core barrel 8 may be a metal such as, without limitation, steel, iron, aluminum, Hastelloy, titanium or any combinations thereof. In embodiments, core barrel 8 may be steel.

As further illustrated in FIG. 2, annular fluid 10 may be disposed between core barrel 8 and synthetic tubing 12. In embodiments, annular fluid 10 may be a liquid used to apply stress and/or pressure to core sample stack 16 during fluid flow analysis of reservoir test sample 2. Stress and/or pressure may be applied during testing in order to better simulate subsurface reservoir conditions of high stress and high pressure. In embodiments, annular fluid 10 may be pressurized by additional laboratory equipment, thereby achieving evenly distributed, radial-inward pressure on core sample stack 16. The amount of pressure may be any value suitable for simulating subsurface pressure conditions in a reservoir may be between, about 1000 psi and about 25000 psi, alternatively between about 3000 psi and 20000 psi, or alternatively between about 10000 psi and 15000 psi. In order to simulate these pressures during fluid flow analysis, reservoir test sample 2 may utilize any suitable amount of annular fluid 10 ranging between about 1 L and about 20 L, alternatively between about 1 L and about 15 L, or alternatively between about 1 L and about 10 L of overburdened fluid. In embodiments, annular fluid 10 may be any suitable hydraulic fluid such as, without limitation, water, oil, or any combinations thereof.

In order to isolate annular fluid 10 from core sample stack 16 during fluid flow analysis, reservoir test sample 2 may utilize synthetic tubing 12. In embodiments, synthetic tubing 12 may be disposed between annular fluid 10 and supporting layers 14. Synthetic tubing 12 may be any suitable material capable of resisting liquids, oils, and/or chemicals, particularly in environments of high pressures and temperatures. Suitable materials may be, without limitation, rubber, synthetic rubber, fluoropolymer elastomer, or any combinations thereof. In embodiments, synthetic tubing 12 may be dimensioned to correspond with core sample stack 16 such that synthetic tubing 12 may fully encase core sample stack 16 and supporting layers 14. In embodiments, synthetic tubing 12 may provide a complete seal for core sample stack 16 such that any and all fluids and/or hydrocarbons within core sample stack 16 may be isolated from annular fluid 10 of reservoir test sample 2 and vice versa.

As further illustrated in FIG. 2, reservoir test sample 2 may comprise supporting layers 14 disposed between core sample stack 16 and synthetic tubing 12. In embodiments, supporting layers 14 may comprise any suitable materials capable of supporting core sample stack 16. In embodiments, supporting layers 14 may comprise a porous screen, a shrink tubing, and a thin metal sheet. The porous screen may be in direct contact with core sample stack 16, with the shrink tubing surrounding the porous screen, and the thin metal sheet surrounding the shrink tubing such that the porous screen may be isolated from synthetic tubing 12. In embodiments, the shrink tubing may be impermeable and malleable tubing and the thin metal sleeve may be foil, or the like. Such support may secure members of core sample stack 16 together, as well as prevent movement within core sample stack 16. Additionally, supporting layers 14 may allow for fluid flow around the periphery of core sample stack 16. Other suitable materials for supporting layers 14 may be, without limitation, steel, vinyl, polyester, brass, aluminum, copper, laminated polyimide, plastics, thermo plastics, or any combinations thereof. In embodiments, supporting layers 14 may be dimensioned to correspond with core sample stack 16 such that supporting layers 14 may fully encase core sample stack 16. In embodiments, supporting layers 14 may comprise a screen, shim stock, heat shrink, or any combinations thereof.

Figure 3:
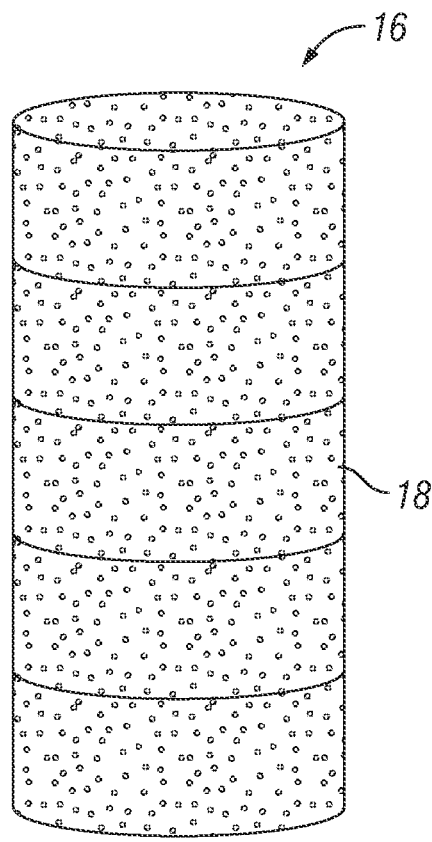
FIG. 3 illustrates an embodiment of a core sample stack from a perspective view.

In embodiments, core sample stack 16 may be disposed about the center of reservoir test sample 2. Core sample stack 16 may be a stack of porous media obtained from a subsurface oil and gas reservoir. FIG. 3 illustrates an embodiment of core sample stack 16 from a perspective view. In embodiments, core sample stack 16 may be any suitable shape and/or size to allow for sufficient testing and/or simulation of fluid flow in an oil and gas reservoir. Further, core sample stack 16 may comprise at least one core segment 18. In embodiments, core sample stack 16 may be assembled such that each core segment 18 may be stacked end-to-end, thus establishing a large pore volume. As illustrated in FIG. 3, core sample stack 16 may be cylindrically shaped and comprise five core segments 18. However, other embodiments may be rectangular or triangular in shape, and may comprise greater than or less than five core segments 18. In embodiments, core sample stack 16 may comprise a single core segment 18. Shape, size, and/or number of core segments 18 may depend on the fluid flow analysis and the testing performed on reservoir test sample 2.

Figure 4:
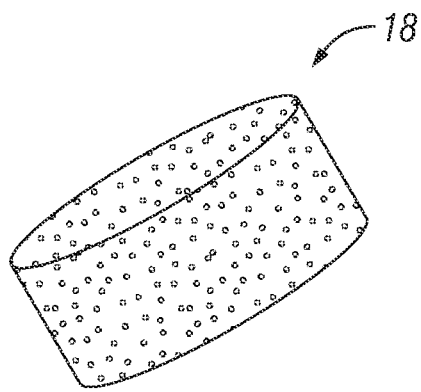
FIG. 4 illustrates an embodiment of a single core segment from a perspective view.

FIG. 4 illustrates a single core segment 18. In embodiments, core segment 18 may comprise unconventional porous media. As such, core segment 18 may have a permeability less than 10 milli-Darcy (mD), alternatively less than 5 mD, or alternatively less than 1 mD. In yet another alternative, the permeability may be less than 10 micro-Darcy ($\mu$D). Core segment 18 may have a porosity ranging from about 1% to about 10%, alternatively from about 2% to about 8%, or alternatively from about 3% to about 6%. In embodiments, core segment 18 may have a porosity in the 5% range. Additionally, core segment 18 may have a water saturation ranging from about 10% to about 40%, alternatively from about 15% to about 35%, or alternatively from about 20% to about 30%. In embodiments, core segment 18 may have a water saturation in the 25% range. With these permeability, porosity, and water saturation characteristics, fluid flow analysis of core sample stack 16 may be accompanied by a series of drawbacks during testing and/or simulation, particularly when using conventional axial-flow lab equipment.

A first drawback may involve the amount of time needed to move fluids such as hydrocarbon streams through core sample stack 16. Moving fluids, particularly in an axial direction at pressure differentials that will not change the characteristics of the fluids, may require a disadvantageous amount of time to displace a single pore volume of fluid through the stack. For instance, displacement of multiple pore volumes by conventional means may take several years to occur, at which point testing and/or simulation is not efficient or cost effective. A second drawback may involve the inability to recognize or evaluate the matrix-fracture regime of fluid flow in core sample stack 16. The matrix-fracture regime may be fluid flow between a matrix and a hydraulic fracture of porous media in a direction orthogonal to the hydraulic fracture axis. The usage of traditional axial-flow equipment may preclude the evaluation of matrix-fracture fluid flow. Therefore, reservoir test sample 2 may be configured such that fluid flow analysis may be possible without these drawbacks.

Figure 5:
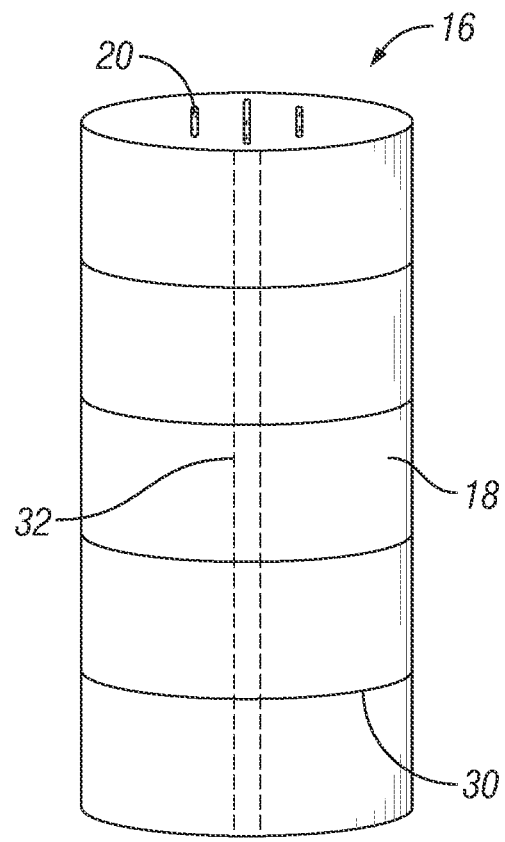
FIG. 5 illustrates an embodiment of a core sample stack comprising core slots from a perspective view.

FIG. 5 illustrates a perspective view of core sample stack 16 with core segments 18 comprising one or more core slots 20. In embodiments, one or more core slots 20 may allow for a 360-degree radial fluid flow from outside to inside core sample stack 16 or vice versa. With this incorporation, a radial matrix fluid flow may be connected to an axial fracture fluid flow within core sample stack 16, thereby allowing fluid flow analysis of both the matrix-fracture regime as well as the fracture regime. Additionally, the incorporation of 360-degree radial fluid flow along with axial fluid flow may minimize the time required to displace a single pore volume of fluid through the stack, such that testing and/or simulation of reservoir test sample 2 may be efficient and cost effective. In embodiments, one or more core slots 20 of each core segment 18, which may be stacked end-to-end, may correspond in number, alignment, and/or size.

Figure 6:
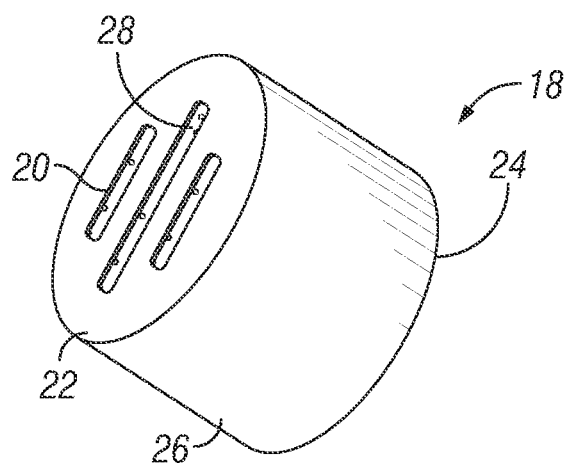
FIG. 6 illustrates an embodiment of a core segment comprising core slots from a perspective view.

FIG. 6 illustrates a single core segment 18 with one or more core slots 20. One or more core slots 20 may be axial fractures created using high-pressure water jet technology disposed in core segment 18 along the longitudinal axis. In embodiments, one or more core slots 20 may comprise any suitable number of slots disposed within core segment 18. In embodiments, one or more core slots 20 may comprise one, three, or five slots. As illustrated in FIG. 6, core segment 18 may comprise three core slots 20. Each core slot 20 may be disposed at any suitable location within core segment 18. In embodiments, each core slot 20 may be at least 0.5 cm from an outer surface 26 of core segment 18, alternatively at least 1 cm from outer surface 26, or alternatively at least 2 cm from outer surface 26. In embodiments, one or more core slots 20 may be evenly distributed within core segment 18. Additionally, one or more core slots 20 may be any suitable length and/or width. The length of each core slot 20 may be any distance which does not exceed the diameter of core segment 18 or a distance equal to the horizontal length of core segment 18. The width of each core slot 20 may be any distance between about 0.1 cm and about 1 cm, alternatively between about 0.1 cm and about 0.5 cm, or alternatively between about 0.1 cm and about 0.25 cm. In embodiments, one or more core slots 20 may extend from an upper surface 22 to a bottom surface 24 of core segment 18. Before testing and/or simulation, each core slot 20 may comprise frac sand 28 which may permit each core slot 20 to have the same hydraulic fracture permeability in the laboratory as that observed in situ in the field. In order to evenly pack frac sand 28 within each core segment 18, vibration techniques may be used during the construction of core sample stack 16. Additionally, frac sand 28 may provide the same or similar permeability in each core slot 20 as a field-based frac may provide in hydraulic fracs in situ.

In further embodiments, core sample stack 16 may comprise separating gaskets 30, as illustrated in FIG. 5. Separating gaskets 30 may be disposed between each core segment 18 of core sample stack 16. Each separating gasket 30 may comprise a pattern of holes corresponding to one or more core slots 20 of core segment 18. In embodiments, separating gaskets 30 may negate flow between core segments 18 of core sample stack 16, as well as negate any flow between the synthetic slabs of nylon media or the other impermeable material that may have been machined to bring the porous media set-up into cylindrical form. Further, separating gaskets 30 may eliminate a matrix-matrix regime of fluid flow as this regime may be insignificant when evaluating reservoir test sample 2. Separating gaskets 30 may be any suitable material capable of resisting this regime of fluid flow including but not limited to rubber, viton, nylon, or any combinations thereof.

In further embodiments, core sample stack 16 may comprise a support rod 32, as illustrated in FIG. 5. Support rod 32 may be disposed about the center of core sample stack 16 in order to provide additional support in maintaining alignment of each core segment 18 during construction of reservoir test sample 2. In embodiments support rod 32 may be dimensioned according to core sample stack 16, such that the length may allow support rod 32 to pass through each core segment 18 of core sample stack 16 and the width may allow support rod 32 to rest within core segment 18 without interfering with the testing and/or simulations that may be performed on reservoir sample 2. In embodiments support rod 32 may be any suitable material capable of supporting core sample stack 16 including, without limitation, stainless steel, aluminum, Hastelloy, or any combinations thereof. In further embodiments, core sample stack 16 may comprise multiple support rods 32 disposed at any location within the stack. Multiple support rods 32 may increase the support provided to core sample stack 16 as well as ensure proper alignment of core segments 18. However, during fluid flow analysis or experimentation of reservoir test sample 2, support rod 32 may be removed.

To further illustrate various illustrative embodiments of the present invention, the following examples are provided.

Example 1

Example 1 demonstrates the results for a reservoir test sample without core slots. The characteristics of unconventional, hydraulically-fractured porous media that may be utilized in a reservoir test sample is shown in Table 1.

TABLE 1

| Parameter | Value |
| --- | --- |
| Permeability | <1 μD |
| Porosity | 5% range |
| Water Saturation | 25% range |

Porous media with the parameter values in Table 1, with a pore volume of at least 200 ml, may require long periods of time to displace one pore volume of fluid through a core sample stack without the incorporation of core slots and absent of radial flow. Time results in relation to permeability of the porous media are shown in Table 2. Result are based on standard axial-flow testing with a fluid viscosity of 0.5 cP and a differential pressure of 3000 psi.

TABLE 2

| Permeability | Time to Displace One Pore Volume of Fluid |
|---|---|
| 1 µD | 29 weeks |
| 20 nD | 1494 weeks |

Based on the results in Table 2, the testing of unconventional, hydraulically-fractured porous media with low permeability using standard axial-flow equipment may result in inefficient timing to displace fluid in a core sample stack, particularly in porous media without core slots.

Example 2

Example 2 demonstrates the results for a reservoir test sample with core slots. The characteristics of unconventional, hydraulically-fractured porous media that may be utilized in a reservoir test sample is the same as the media used in Example 1 (parameter values shown in Table 1). However, the porous media in this example incorporates core slots to allow for radial fluid flow in addition to axial fluid flow. Time results in relation to permeability of the porous media are shown in Table 3. Result are based on the new radial/axial fluid flow testing with a fluid viscosity of 0.5 cP at 3000 psi differential pressure.

TABLE 3

| Permeability | Time to Displace One Pore Volume of Fluid |
|---|---|
| 1 µD | 17 hours |
| 20 nD | 5 weeks |

Based on the results in Table 3, the testing of unconventional, hydraulically-fractured porous media with the incorporation of core slots may result in efficient timing to displace fluid in a core sample stack.

Although the present invention and its advantages have been described in detail, it should be understood that various changes, substitutions and alterations may be made herein without departing from the spirit and scope of the invention as defined by the appended claims.

What is claimed is:

1. A fluid flow analysis system, comprising:
   a reservoir test sample, comprising:
      a core barrel, wherein the core barrel is the outer most portion of the reservoir test sample;
      annular fluid, wherein the annular fluid is pressurized to between 1,000 psi and 25,000 psi, and further wherein the annular fluid comprises an amount between 1 liter and 20 liters;
      a synthetic tubing, wherein the annular fluid is disposed between the core barrel and the synthetic tubing;
      a plurality of supporting layers, wherein the plurality of supporting layers comprises a porous screen, a shrink tubing, and a thin metal sheet, wherein the shrink tubing surrounds the porous screen and the thin metal sheets surrounds the shrink tubing, wherein the porous screen is isolated from the synthetic tubing, and further wherein the synthetic tubing is disposed between the annular fluid and the supporting layers; and
      a core sample stack, wherein the core sample stack comprises unconventional, hydraulically-fractured porous media, wherein the core sample stack is cylindrically shaped and comprises five core segments wherein each core segment comprises a permeability less than 10 mill-Darcy and wherein each core segment comprises a plurality of core slots, wherein the plurality of core slots are stacked end-to-end, and further wherein the supporting layers are disposed between the synthetic tubing and the core sample stack;
   wherein the annular fluid, the synthetic tubing, the supporting layers, and the core sample stack are disposed within the core barrel;
   further wherein the synthetic tubing fully encases the core sample stack and the supporting layers, and wherein the synthetic tubing completely seals the core sample stack; and
   further wherein the porous screen is in direct contact with the core sample stack.

2. A fluid flow analysis system of claim 1, wherein the fluid flow analysis system incorporates with additional laboratory equipment.

3. A fluid flow analysis system of claim 1, wherein the core sample stack is disposed about a center of the fluid flow analysis system.

4. A fluid flow analysis system of claim 3, wherein the plurality of core slots extends from an upper surface of the five core segments to a bottom surface of the five core segments.

5. A fluid flow analysis system of claim 1, further comprising a plurality of flow heads, wherein at least one flow head of the plurality of flow heads is disposed at each end of the fluid flow analysis system, and further wherein the plurality of flow heads provides a seal separating annular overburden pressure from pore pressure in the reservoir test sample.

6. A fluid flow analysis system of claim 1, wherein the reservoir test sample is placed in an over with a temperature of 400 degrees Fahrenheit for analysis.

7. A fluid flow analysis system of claim 1, wherein the plurality of core slots allows for a 360-degree radial fluid flow from outside to inside the core sample stack, and further wherein a radial matrix fluid flow is connected to an axial fracture fluid flow within the core sample stack allowing a fluid flow analysis of the matrix-fracture regime and the fracture regime.

8. A fluid flow analysis system of claim 1, wherein permeability of the core sample stack is less than 1 µD.

9. The fluid flow analysis system of claim 1, wherein the core sample stack comprises a plurality of separating gaskets, wherein the plurality of separating gaskets is disposed between each of the core segments, and further wherein each of the plurality of separating gaskets comprises a pattern of holes corresponding to one or more core slots.

10. The fluid flow analysis system of claim 1, wherein the core sample stack further comprises a support rod, wherein the support rod is disposed about the center of the core sample stack and maintains alignment of each core segment during construction of the reservoir core sample.

11. The fluid flow analysis system of claim 10, wherein the core sample stack comprises a plurality of support rods.

\* \* \* \* \*